US009426988B2

(12) United States Patent
Ruiz Ballesteros et al.

(10) Patent No.: US 9,426,988 B2
(45) Date of Patent: Aug. 30, 2016

(54) TABLET FOR DELIVERING VOLATILE SUBSTANCES AND EVAPORATION DEVICE FOR USE WITH SAID TABLET

(71) Applicant: ZOBELE ESPANA, S.A., Barcelona (ES)

(72) Inventors: Julio Cesar Ruiz Ballesteros, Barcelona (ES); Cedric Gobber, Barcelona (ES); Montserrat Riera Giner, Barcelona (ES)

(73) Assignee: ZOBELE ESPANA, S.A., Barcelona (ES)

( * ) Notice: Subject to any disclaimer, the term of this patent is extended or adjusted under 35 U.S.C. 154(b) by 295 days.

(21) Appl. No.: 14/080,232

(22) Filed: Nov. 14, 2013

(65) Prior Publication Data

US 2014/0130398 A1    May 15, 2014

(30) Foreign Application Priority Data

Nov. 14, 2012 (EP) .................................... 12382449

(51) Int. Cl.
| | |
|---|---|
| *A61L 9/04* | (2006.01) |
| *A01N 25/34* | (2006.01) |
| *A01M 1/20* | (2006.01) |
| *A61L 9/014* | (2006.01) |

(52) U.S. Cl.
CPC ............ *A01N 25/34* (2013.01); *A01M 1/2055* (2013.01); *A01M 1/2077* (2013.01); *A61L 9/014* (2013.01); *A61L 9/04* (2013.01); *A61L 2209/133* (2013.01)

(58) Field of Classification Search
CPC ............... A01N 25/34; A01M 1/2061; A61L 2209/133
USPC .......................................................... 239/60
See application file for complete search history.

(56) References Cited

U.S. PATENT DOCUMENTS

2003/0175320 A1* 9/2003 Weiser .................. A01N 25/34
424/411

FOREIGN PATENT DOCUMENTS

| DE | 9017257 | 3/1991 |
|---|---|---|
| GB | 2211415 | 7/1989 |
| JP | 2002253649 | 9/2002 |

OTHER PUBLICATIONS

European Search Report—Application No. EP13191379.

* cited by examiner

*Primary Examiner* — Kevin Joyner
(74) *Attorney, Agent, or Firm* — Lucas & Mercanti, LLP

(57) ABSTRACT

Tablet (1) for delivering volatile substances comprising an active ingredient permeated in it, and which is characterized in that it comprises a handle (2) for its placement and removal from an evaporation device (6). Preferably, said handle comprises at least one protrusion (3) that can be housed in a complementary cavity (4) of the evaporation device (6).
It permits the tablet, after it has been spent, to be easily removed without using any other element such as, for example, another tablet or a tool.

7 Claims, 3 Drawing Sheets

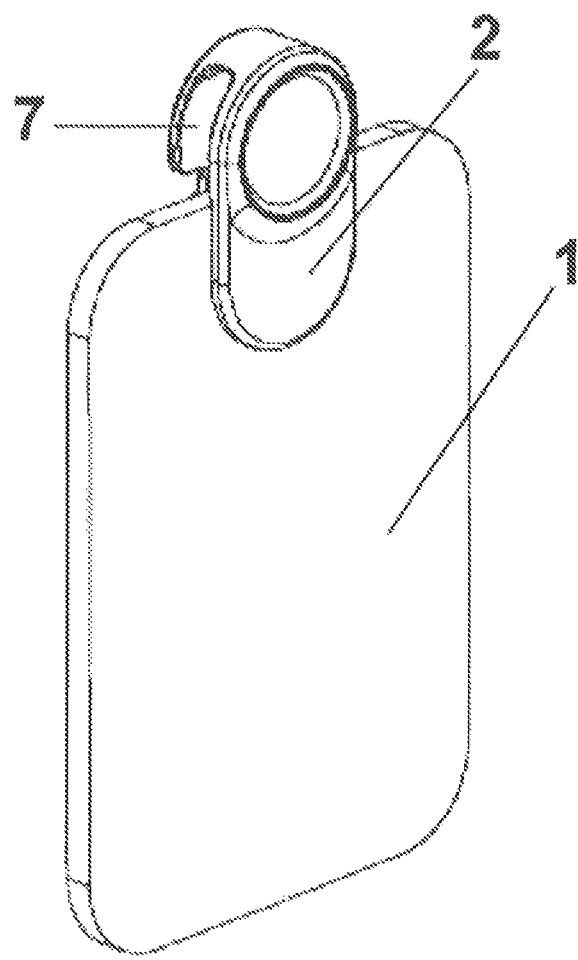

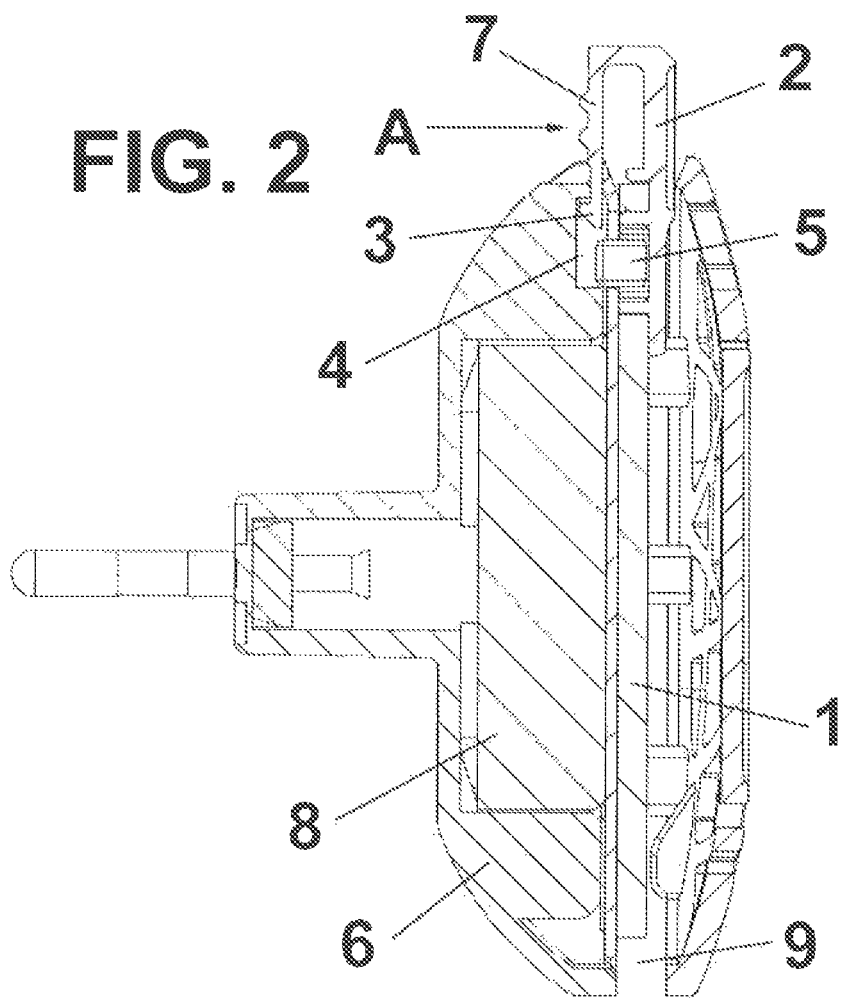

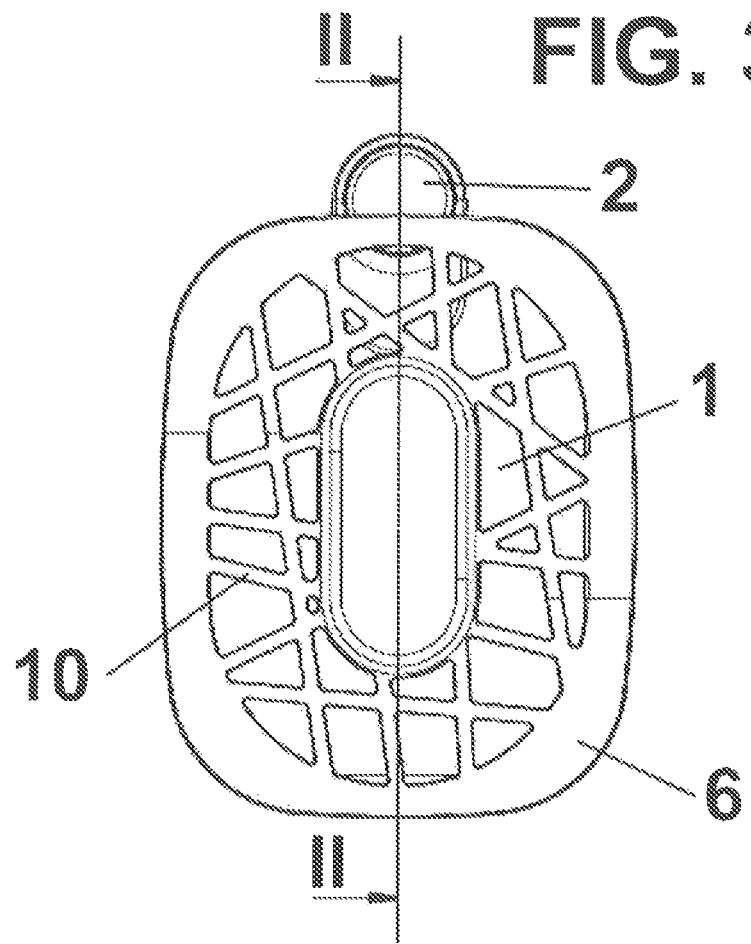

TABLET FOR DELIVERING VOLATILE SUBSTANCES AND EVAPORATION DEVICE FOR USE WITH SAID TABLET

CROSS-REFERENCE TO RELATED APPLICATIONS

This application claims the priority of EP 12382449.2 filed Nov. 14, 2012, which is incorporated by reference herein.

The present invention refers, in a first aspect, to a tablet for delivering volatiles substances present in said tablet, for example, an insecticide.

According to a second aspect, the present invention refers to an evaporation device for its use with a tablet according to the first aspect of the present invention.

BACKGROUND OF THE INVENTION

The use of tablets for delivering volatile substances such as insecticides or air fresheners is known in the state of art. To this end, the tablets are permeated in an active ingredient, for example an insecticide.

In order to be used, the tablet is inserted in an evaporation device in such a way that said evaporation device heats the tablet, causing the evaporation of the insecticide or air freshener.

Tablets of this type currently known in the art are designed to last one night, that is, approximately eight hours. Furthermore, all of them have some very similar dimensions and most of them are made of cellulose.

A drawback of the tablets currently known in the art is the difficulty of removing them from the evaporation device after using it, thus it being common the use of another tablet to be able to remove the previously spent tablet.

If another tablet is not used, it is necessary to use a tool, creating an unsafe situation for the user and for the device.

From the point of view of manufacturing the evaporation device, as all the tablets currently in the market have very similar dimensions, a user can choose from among different tablets, even though they are not specifically designed to be used in the evaporation device. This could result in safety problems, because the materials and active ingredient of the alternative tablet might not be adequate for being used in the operating conditions of the evaporation device.

Therefore, a first objective of the tablet for delivering volatile substances of the present invention is to provide a table that, after it has been spent, can be comfortably removed without using any other element, such as for example, another tablet or a tool, and at the same time is childproof, in such a way that a child will not be able to remove said tablet.

A second objective of the present invention is to obtain a tablet that can only be used in one evaporation device, in such a way that the manufacturer of the evaporation device can avoid tablets from being used that are not specifically designed for its device.

A third objective of the present invention is to obtain a tablet that lasts much longer than the tablets currently in use, in combination with a given evaporation device.

DESCRIPTION OF THE INVENTION

Said drawbacks can be solved with the tablet for delivering volatile substances and the evaporation device of the invention, together with other advantages that are described below.

The tablet for delivering volatile substances comprises an active ingredient permeated in it and is characterised in that it comprises a handle for its placing in and removal from the evaporation device.

Advantageously, said handle comprises at least one protrusion that can be housed in a complementary cavity of an evaporation device.

Furthermore, the tablet of the present invention preferably comprises at least one hole for introducing a fastening pin of said handle.

Advantageously, said handle is made of an elastic material, plastic for example, and comprises an elastic tab joined at one of its ends to the rest of the handle and said protrusion being located on the other end, in such a way that it is possible to remove the tablet of the evaporation device by pressing on said elastic tab.

According to a second aspect, the present invention refers to an evaporation device for use with a table for delivering volatile substances according to the first aspect, which comprises a heating surface for evaporating the active ingredient permeated in the tablet, and is characterised in that it comprises a housing for said tablet with dimensions larger than said heating surface, so that in its use position a portion of said tablet is not in direct contact with said heating surface.

According to a preferred embodiment, the dimensions of said housing are between 1.5 and 3 times larger than the dimensions of said heating surface.

Thanks to the tablet and the evaporation device of the present invention, the following advantages are also obtained:

- the tablet is always placed correctly in the evaporation device;
- a good contact is ensured between the tablet and the evaporation device;
- it prevents the user from using tablets that are not defined for a particular evaporation device, avoiding a malfunction of the system comprising the evaporation device and the tablet.
- it is childproof, given that sufficient pressure must be exerted to be able to remove the tablet; and
- it provides an easy and safe manner for inserting and removing the tablet without directly touching the permeated portion.

BRIEF DESCRIPTION OF THE DRAWINGS

For better understanding the above explanation and for the only purpose of providing an example, some non-limiting drawings are included that schematically shown a practical embodiment.

FIG. 1 is an exploded perspective view of the system for delivering volatile substances of the present invention;

FIG. 2 is a side elevation view of a cross-section of the evaporation device of the present invention especially designed to be used with the tablet for delivering volatile substances of the present invention, with the tablet in its use position inside the evaporation device; and FIG. 3 is a front elevation view of the evaporation device of the present invention.

DESCRIPTION OF A PREFERRED EMBODIMENT

The tablet for delivering volatile substances, identified overall as reference 1, comprises a handle 2, for example of injected plastic material.

Said tablet 1 is placed inside an evaporation device 6, that comprises a housing 9 for said tablet 1 and a heating surface 8 that heats the tablet 1, causing the evaporation of volatile substances from an active ingredient permeated in the tablet 1, for example an insecticide. These volatile substances are dispersed into the environment through a screen 10 of said evaporation device 6.

Said handle 2 is fixed to the tablet 1 by means of a fastening pin 5 that is housed in a complementary hole of said tablet 1, thus creating a solid fastening between the handle 2 and the tablet 1 and avoiding the rotation of the handle 2 with respect to said orifice.

The handle 2 also comprises an elastic tab 7 joined at its top end to the handle 2. Furthermore, said elastic tab 7 comprises on its bottom end a protrusion 3 that is housed inside the cavity 4 complementary with the evaporation device 6, retaining it.

When the user engages the tablet 1 through the handle 2 inside the evaporation device 6, a coupling noise is produced when the protrusion 3 of the elastic tab 7 couples inside of cavity 4. This way, the users can be fully certain that the tablet 1 is positioned in its correct position.

In this contact position, the tablet 1 engages in its housing 9 in a suitable manner for obtaining a good contact with the heating surface 8 and obtaining an adequate evaporation.

In the case a tablet 1 is used that is not specifically designed for this evaporation device 6, tablet 1 would either not correctly engage in said housing 9, thus causing incorrect evaporation, or it could even fall out of evaporation device 6, given that said housing is open at the bottom, as can be seen in FIG. 2.

Furthermore, once the tablet 1 is engaged in its use position, it is necessary to apply pressure enough (indicated as arrow A in FIG. 2) on the tab to be able to remove it. This pressure has been designed so that a child cannot apply it, only an adult.

Just as has been indicated above, the tablet 1 is permeated with an active ingredient that will be mixed with a suitable solvent and a blue ink, with the ink evaporating at the same time as the active ingredient. This is done for indicating how spent the tablet 1 is, such that when tablet 1 is completely white, it is time to change it.

On the other hand, most of the tablets found in the market have very similar dimensions, for example 22×35 mm, and contain a similar amount of active ingredients so that the tablet can last about eight hours.

Furthermore, the majority of the heating surfaces of the evaporation devices heat at approximately the same temperature (120-160° C.) and have the same dimensions as the tablet.

However, in the case of the present invention the size of tablet 1 is greater than the dimensions of said heating surface 6, for example between 1.5 and 3 times larger, that is, the housing 9 for said tablet 1 is larger than said heating surface 6, in such a way that only a portion of tablet 1 will be in contact with the heating surface 6 and will be heated directly.

This feature provides a correct evaporation index in the contact area with the heating surface 6, and provides an extra capacity for active ingredient in the area of the tablet that is not directly heated, which provides a continuous flow of active ingredient and ink towards the area directly heated by means of capillary action. Therefore, a much longer duration is obtained with respect to conventional tablets, for example 100 to 180 hours of protection, providing a rational and constant evaporation index.

Even though reference has been made to a specific embodiment of the invention, it is obvious to a person skilled in the art that the tablet for delivering volatile substances described herein is susceptible to numerous variations and modifications, and that all of the details mentioned can be substituted for other technically equivalent ones without departing from the scope of protection defined by the attached claims.

The invention claimed is:

1. A tablet for delivering volatile substances, the tablet comprising:
   a portion made of one or more volatile substances including an active ingredient, the portion including a straight edge and a hole proximate the straight edge, wherein the portion is adapted to deliver the volatile substances into a surrounding environment when heated; and
   a handle for placement of the tablet into and removal of the tablet from an evaporation device, the handle including a fastening pin adapted to fit into the hole and an element adapted to fit into a position of contact with the straight edge;
   wherein:
      the handle is in direct contact with the portion, and the position of the element prevents the handle from rotating, when the pin is disposed in the hole.

2. The tablet for delivering volatile substances according to claim 1, wherein said handle comprises at least one protrusion adapted to hold the handle and tablet within the evaporation device.

3. The tablet for delivering volatile substances according to claim 2, wherein said handle comprises a first end and a second end, said handle further comprising an elastic tab joined to the handle at the first end, said protrusion being located at the second end.

4. The tablet for delivering volatile substances according to claim 1, wherein said handle is made of an elastic material.

5. The tablet for delivering volatile substances according to claim 4, wherein said handle is made of plastic.

6. An evaporation device comprising:
   a housing including a first side, a second side, and a space between the first and second sides;
   a tablet disposed within the space of the housing, the tablet comprising:
      a portion comprising one or more volatile substances and an active ingredient; and
      a handle connected to and in direct contact with the portion, the handle comprising a protrusion;
   a heating surface for evaporating the active ingredient of the tablet, the heating surface disposed on the first side of the housing;
   a cavity different from the housing, the cavity being adapted to receive the protrusion, the cavity being located on the first side of the housing; and
   a screen disposed on the second side of the housing, the screen comprising a plurality of openings adapted to permit volatile substances to travel from the space within the housing to an environment outside the evaporation device.

7. The evaporation device according to claim 6, wherein a first dimension of said housing is between 1.5 and 3 times larger than a second dimension of said heating surface.

* * * * *